(12) United States Patent
Smith (10) Patent No.: US 8,353,875 B2
(45) Date of Patent: Jan. 15, 2013

(54) ACCESS APPARATUS WITH SHALLOW ZERO CLOSURE VALVE

(75) Inventor: Robert C. Smith, Middletown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/204,804

(22) Filed: Aug. 8, 2011

(65) Prior Publication Data

US 2011/0295076 A1 Dec. 1, 2011

Related U.S. Application Data

(63) Continuation of application No. 12/128,698, filed on May 29, 2008, now Pat. No. 8,002,750.

(60) Provisional application No. 60/932,576, filed on May 31, 2007.

(51) Int. Cl.
*A61M 5/178* (2006.01)

(52) U.S. Cl. .................................. 604/167.03

(58) Field of Classification Search ........... 606/185.108; 304/164.01, 168.01, 167.01–167.06; 251/149.1; 137/515
See application file for complete search history.

(56) References Cited

U.S. PATENT DOCUMENTS

| | | | |
|---|---|---|---|
| 4,177,814 A | 12/1979 | Knepshield |
| 4,436,519 A | 3/1984 | O'Neill |
| 4,535,819 A | 8/1985 | Atkinson |
| 5,010,925 A | 4/1991 | Atkinson |
| 5,141,498 A | 8/1992 | Christian |
| 5,180,373 A | 1/1993 | Green |
| 5,263,944 A | 11/1993 | Vidal |
| 5,269,763 A | 12/1993 | Boehmer et al. |
| 5,282,790 A | 2/1994 | Clement |
| 5,300,033 A | 4/1994 | Miller |
| 5,300,035 A | 4/1994 | Clement |
| 5,312,362 A | 5/1994 | Pfolsgraf et al. |
| 5,324,270 A | 6/1994 | Kayan et al. |
| 5,330,437 A | 7/1994 | Durman |
| 5,354,280 A | 10/1994 | Haber et al. |
| 5,356,394 A | 10/1994 | Farley et al. |

(Continued)

FOREIGN PATENT DOCUMENTS

EP 1520537 A 4/2005

(Continued)

OTHER PUBLICATIONS

European Search Report for corresponding EP08251870 date of mailing is Sep. 22, 2008 (3 pages).

*Primary Examiner* — Christopher D Koharski (57) ABSTRACT

A surgical access assembly including a housing, an elongate access member and a zero closure valve including a valve periphery having a collar, a tapered segment extending inwardly from the collar and a second segment extending contiguously from the tapered segment. First and second lips depend from the second segment of the zero closure valve and define lip edges which are in approximated closed relation when the zero closure valve is in the closed position to define a slit. The first and second lips each include a proximal lip surface having an outer surface portion and an inner surface portion interconnected by a curved surface. A support rib depends from the proximal lip surface of each of the first and second lips to define a gap therebetween to be in spaced relation when the valve is in the closed position and being positioned to contact the surgical instrument during insertion through the first and second lips.

12 Claims, 10 Drawing Sheets

U.S. PATENT DOCUMENTS

| | | | |
|---|---|---|---|
| 5,380,288 A | 1/1995 | Hart et al. | |
| 5,385,552 A | 1/1995 | Haber et al. | |
| 5,391,153 A | 2/1995 | Haber et al. | |
| 5,401,248 A | 3/1995 | Bencini | |
| 5,417,705 A | 5/1995 | Haber et al. | |
| 5,431,667 A | 7/1995 | Thompson et al. | |
| 5,441,486 A | 8/1995 | Yoon | |
| 5,443,452 A | 8/1995 | Hart et al. | |
| 5,492,304 A | 2/1996 | Smith et al. | |
| 5,496,280 A | 3/1996 | Vandenbroek | |
| 5,584,850 A | 12/1996 | Hart et al. | |
| 5,603,702 A | 2/1997 | Smith et al. | |
| 5,613,954 A | 3/1997 | Nelson et al. | |
| 5,628,732 A * | 5/1997 | Antoon et al. | 604/167.06 |
| 5,640,977 A | 6/1997 | Leahy et al. | |
| 5,643,301 A | 7/1997 | Mollenauer | |
| 5,657,963 A | 8/1997 | Hinchliffe et al. | |
| 5,709,664 A | 1/1998 | Vandenbroek et al. | |
| 5,788,676 A | 8/1998 | Yoon | |
| 5,803,919 A | 9/1998 | Hart et al. | |
| 5,813,409 A | 9/1998 | Leahy et al. | |
| 5,820,600 A | 10/1998 | Carlson et al. | |
| 5,820,604 A | 10/1998 | Fox et al. | |
| 5,820,606 A | 10/1998 | Davis et al. | |
| 5,857,999 A | 1/1999 | Quick et al. | |
| 5,872,812 A | 2/1999 | Saito et al. | |
| 5,906,595 A | 5/1999 | Powell et al. | |
| 5,913,847 A | 6/1999 | Yoon | |
| 5,989,232 A | 11/1999 | Yoon | |
| 5,989,233 A | 11/1999 | Yoon | |
| 6,066,117 A | 5/2000 | Fox et al. | |
| D426,635 S | 6/2000 | Haberland | |
| 6,083,203 A | 7/2000 | Yoon | |
| 6,086,603 A | 7/2000 | Termin et al. | |
| 6,123,689 A | 9/2000 | To et al. | |
| D449,887 S | 10/2001 | Haberland | |
| 6,551,282 B1 | 4/2003 | Exline | |
| 6,595,946 B1 | 7/2003 | Pasqualucci | |
| 6,702,255 B2 | 3/2004 | Dehdashtian | |
| 7,001,404 B1 | 2/2006 | Chin | |
| 7,011,314 B2 | 3/2006 | McFarlane | |
| 7,112,185 B2 | 9/2006 | Hart et al. | |
| 7,153,319 B1 | 12/2006 | Haberland et al. | |
| 7,163,525 B2 | 1/2007 | Franer | |
| 7,169,130 B2 | 1/2007 | Exline et al. | |
| D537,941 S | 3/2007 | Haberland | |
| 7,300,399 B2 | 11/2007 | Bonadio et al. | |
| 7,393,322 B2 | 7/2008 | Wenchell | |
| 7,789,861 B2 | 9/2010 | Franer | |
| 2002/0010424 A1 | 1/2002 | Dennis | |
| 2002/0107484 A1 | 8/2002 | Dennis | |
| 2002/0128602 A1 | 9/2002 | Adams | |
| 2004/0015185 A1 | 1/2004 | Ewers | |
| 2004/0171990 A1 | 9/2004 | Dennis | |
| 2004/0204682 A1* | 10/2004 | Smith | 604/167.06 |
| 2005/0033342 A1 | 2/2005 | Hart | |
| 2005/0043682 A1 | 2/2005 | Kucklick | |
| 2005/0077688 A1 | 4/2005 | Voegele | |
| 2005/0131349 A1 | 6/2005 | Albrecht | |
| 2005/0212221 A1 | 9/2005 | Smith et al. | |
| 2005/0216028 A1 | 9/2005 | Hart | |
| 2005/0222582 A1 | 10/2005 | Wenchell | |
| 2006/0047284 A1 | 3/2006 | Gresham | |
| 2006/0229565 A1 | 10/2006 | Dennis | |
| 2006/0247673 A1 | 11/2006 | Voegele | |
| 2006/0264991 A1 | 11/2006 | Johnson | |
| 2007/0004968 A1 | 1/2007 | Bonadio | |
| 2007/0088277 A1 | 4/2007 | McGinley | |
| 2007/0244426 A1 | 10/2007 | Hart | |

FOREIGN PATENT DOCUMENTS

| | | |
|---|---|---|
| EP | 1 707 133 | 10/2006 |
| EP | 1 709 918 | 10/2006 |
| EP | 2 042 114 | 4/2009 |
| EP | 2 087 846 | 8/2009 |
| WO | 2008/045744 | 4/2008 |
| WO | 2008/093313 | 8/2008 |

* cited by examiner

ACCESS APPARATUS WITH SHALLOW ZERO CLOSURE VALVE

CROSS REFERENCE TO RELATED APPLICATIONS

The present application is a continuation application of U.S. Ser. No. 12/128,698, filed May 29, 2008 now U.S. Pat. No. 8,002,750, which claims the benefit of and priority to U.S. Provisional Patent Application No. 60/932,576, filed on May 31, 2007, the entire contents of which are incorporated herein by reference.

BACKGROUND

1. Technical Field

The present disclosure relates to a surgical access apparatus including an instrument seal and a low profile zero closure valve.

2. Description of the Related Art

Minimally invasive and laparoscopic procedures generally require that any instrumentation inserted into the body is sealed, i.e., provisions must be made to ensure that gases and/or fluids do not enter or exit the body through an endoscopic incision, such as, for example in surgical procedures where the surgical region is insufflated. For such procedures, the introduction of a tube into anatomical cavities, such as the peritoneal cavity, is usually accomplished by use of a system incorporating a trocar and cannula assembly. Since the cannula is in direct communication with the interior of the peritoneal cavity, insertion of the cannula into an opening in the patient's body to reach the inner abdominal cavity should be adapted to maintain a fluid tight interface between the abdominal cavity and the outside atmosphere. In view of the need to maintain the atmospheric integrity of the inner area of the cavity, a seal assembly for a cannula, which permits introduction of a wide range of surgical instrumentation and maintains the atmospheric integrity of the inner area of the cavity, is desirable. In addition, closure of the passageway of the cannula should be readily effected upon removal of the instrument.

SUMMARY

Accordingly, a surgical access assembly for use with a surgical access device includes a housing defining a central longitudinal axis, an elongate access member extending from the housing whereby the housing and the access member having a longitudinal passage dimensioned to permit passage of a surgical instrument, an instrument seal disposed within the housing and being adapted to establish a substantial fluid tight seal about the instrument and a zero closure valve mounted relative to the housing and being adapted to assume an open condition upon passage of the surgical instrument and a substantially closed position in the absence of the instrument. The zero closure valve includes a valve periphery and first and second lips depending from the valve periphery. The first and second lips have lip edge surfaces in juxtaposed relation to define a slit when the valve is in the closed position thereof. At least one of the lips has a general arcuate internal lip surface leading to the lip edge surface to define a sloping configuration dimensioned to facilitate passage of the surgical instrument through the valve. Each of the first and second lips may define a general arcuate lip surface. In one embodiment, the internal arcuate lip surface of each of the first and second lips includes an outer surface portion arranged at a first angle relative to the longitudinal axis of the seal housing and an inner surface portion arranged at a second angle relative to longitudinal axis and being different from the first angle. The first angle is greater than the second angle.

The internal arcuate lip surface of each of the first and second lips defines an asymmetric configuration. Each of the first and second lips includes a support rib depending from the general arcuate lip surface. The support rib may be positioned to contact the surgical instrument during insertion therethrough. The support ribs may be in spaced relation when the valve is in the substantially closed position thereof.

The valve periphery may include a valve collar and a tapered segment extending inwardly from the valve collar. The valve periphery includes a second segment extending contiguously from the tapered segment. The second segment may be in general perpendicular relation to the longitudinal axis.

BRIEF DESCRIPTION OF THE DRAWINGS

The foregoing features of the present disclosure will become more readily apparent and will be better understood by referring to the following detailed description of preferred embodiments, which are described hereinbelow with reference to the drawings wherein.

DETAILED DESCRIPTION OF PREFERRED EMBODIMENTS

The access apparatus of the present disclosure is capable of accommodating instruments of varying diameters, e.g., from 5 mm to 15 mm, by providing a gas tight seal with each instrument when inserted. The access apparatus incorporates a seal assembly which establishes and maintains a fluid tight interface about instrumentation to preserve the atmospheric integrity of a surgical procedure from gas and/or fluid leakage. The access apparatus further includes a zero-closure valve having a reduced or shallow dimension which closes in the absence of an inserted instrument to prevent gases from escaping through the access apparatus to maintain the integrity of the underlying insufflated peritoneal cavity.

Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation".

By virtue of its features, the seal assembly and the zero-closure valve further defines a substantially reduced profile when assembled together and mounted to a cannula assembly. This reduced profile advantageously increases the working length of instruments introduced into the body cavity through the cannula assembly. In addition, the reduced profile permits enhanced angulation of a surgical instrument relative to the seal housing axis.

In the following description, as is traditional the term "proximal" refers to the portion of the instrument closest to the operator while the term "distal" refers to the portion of the instrument remote from the operator.

Figures 1, 2:
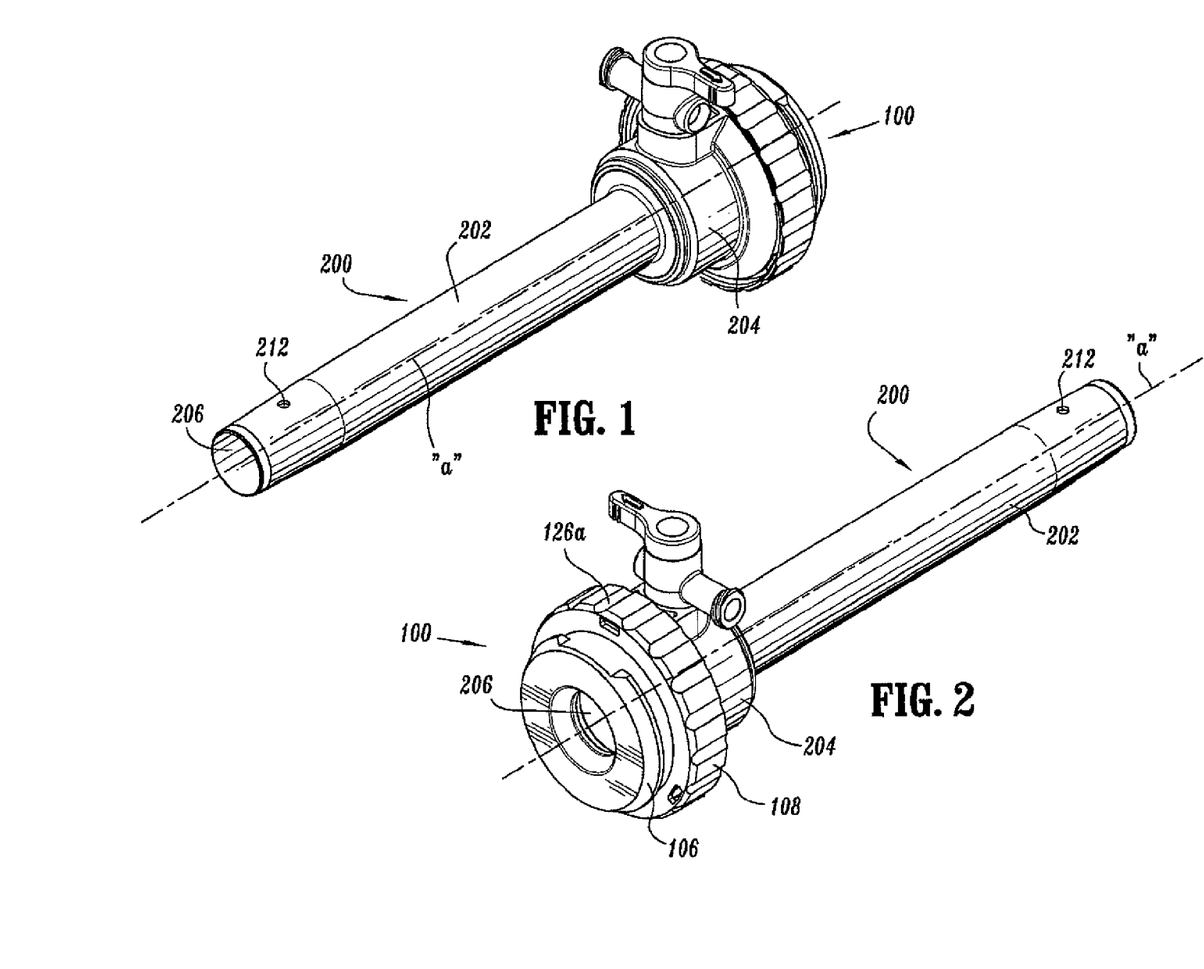
FIGS. 1-2 are perspective views of an access apparatus including a cannula assembly, an instrument seal assembly and a zero closure valve incorporated into the cannula assembly in accordance with the principles of the present disclosure.

Referring now to the drawings, in which like reference numerals identify identical or substantially similar parts throughout the several views, FIGS. 1-2 illustrates an access apparatus 10 incorporating a seal assembly 100 mounted to cannula assembly 200. Cannula assembly 200 may be any conventional cannula suitable for the intended purpose of accessing a body cavity and permit introduction of instruments therethrough. Cannula assembly 200 is particularly adapted for use in laparoscopic surgery where the peritoneal cavity is insufflated with a suitable gas, e.g., $CO_2$, to raise the cavity wall from the internal organs therein. Cannula assembly 200 is typically used with an obturator assembly (not shown) which is a sharp pointed instrument positionable within the passageway of the cannula assembly 200. The obturator assembly is utilized to penetrate the abdominal wall and then subsequently removed from the cannula assembly 200 to permit introduction of the surgical instrumentation utilized to perform the procedure.

With reference to FIGS. 1-4, cannula assembly 200 includes cannula sleeve 202 and cannula housing 204 mounted to an end of the sleeve 202. Any means for mounting cannula sleeve 202 to cannula housing 204 are envisioned including threaded arrangements, bayonet coupling, snap-fit arrangements, adhesives, etc. Cannula sleeve 2-2 and cannula housing 204 may be integrally formed. Cannula sleeve 202 and cannula housing 204 define a longitudinal axis "a" extending along the length of sleeve 202. Sleeve 202 further defines an internal longitudinal passage 206 dimensioned to permit passage of surgical instrumentation. Sleeve 202 defines collar 208 which is mounted to cannula housing 202 and an inner tapered wall 210 adjacent the collar 208. The sloped configuration of tapered wall 210 may assist in guiding the inserted instrument into longitudinal passage 206. Adjacent the distal end of cannula sleeve 202 is aperture 212 which extends through the wall of the sleeve 202. Aperture 212 permits passage of insufflation gases through cannula sleeve 202 during the surgical procedure. Sleeve 202 may be formed of stainless steel or other rigid materials such as a polymeric material or the like. Sleeve 202 may be clear or opaque. The diameter of sleeve 202 may vary, but, typically ranges from about 10 mm to about 15 mm for use with the seal assembly 100 of the present disclosure.

Cannula housing 204 includes port opening 214 and luer fitting 216 positioned within the port opening 214. Luer fitting 216 is adapted for connection to a supply of insufflation gaseous is conventional in the art and incorporates valve 218 to selectively open and close the passage of the luer fitting 216. Cannula housing 204 further includes duckbill or zero closure valve 220.

Figure 4:
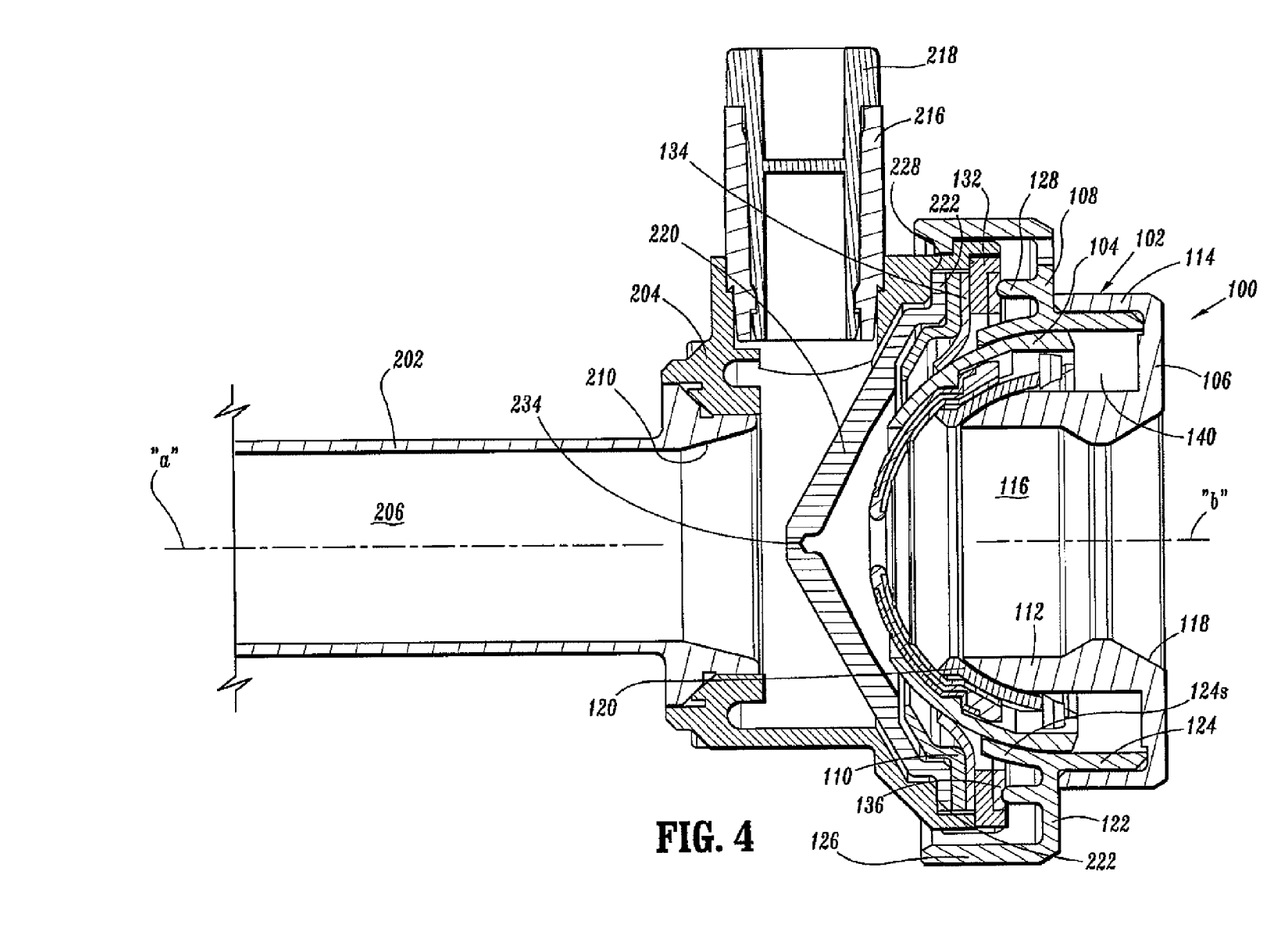
FIG. 4 is a side cross-sectional view of the cannula and instrument seal assemblies.
Figure 5A:
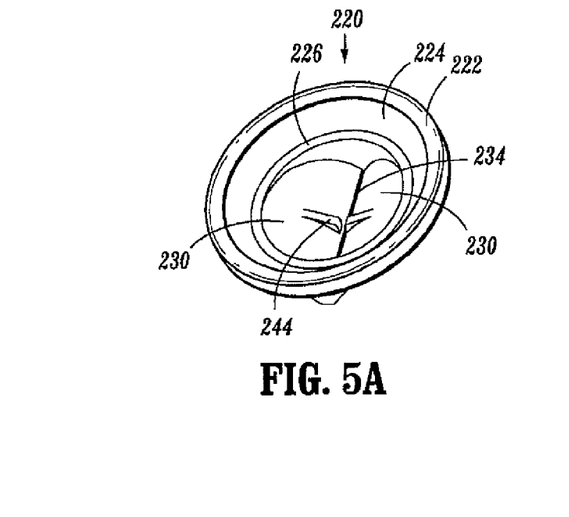
FIG. 5A is a perspective view of the zero closure valve.
Figure 5B:
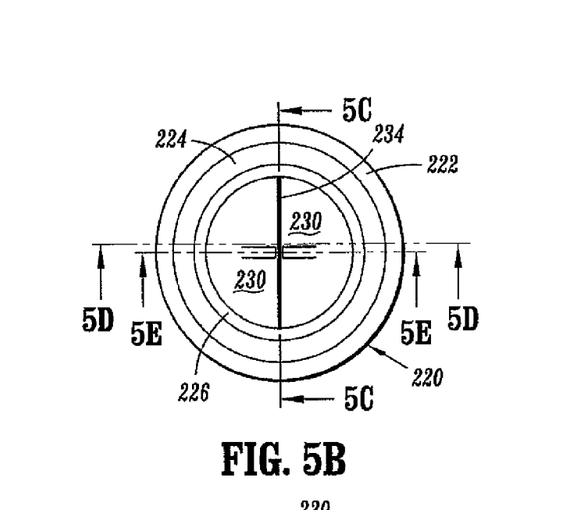
FIG. 5B is a top plan view of the zero closure valve.
Figure 5C:
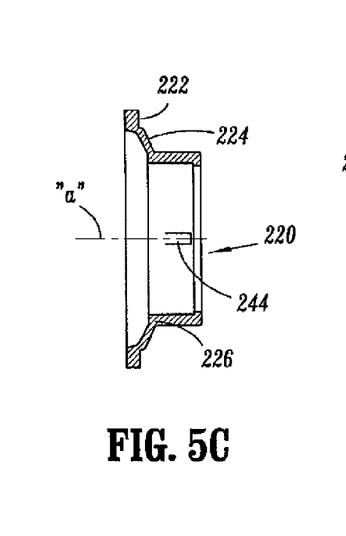
FIG. 5C is a cross-sectional view of the zero closure seal taken along the lines 5C-5C of FIG. 5B.
Figure 5D:
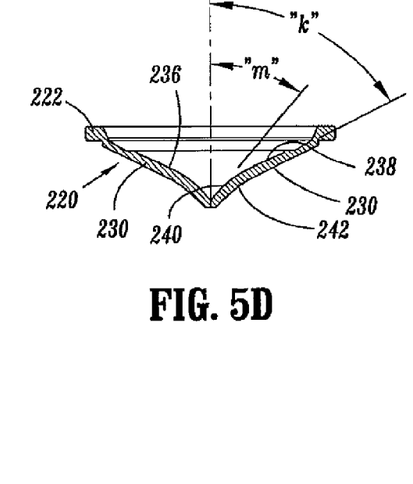
FIG. 5D is a cross-sectional view of the zero closure seal taken along the lines 5D-5D of FIG. 5B.
Figure 5E:
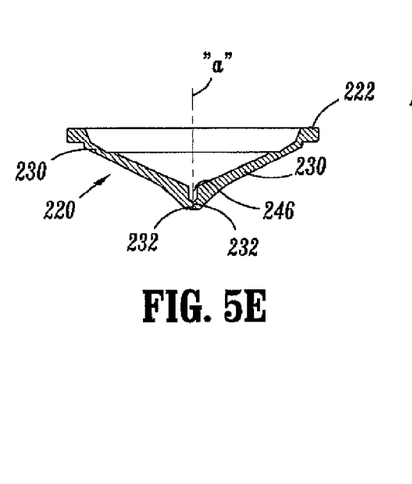
FIG. 5E is a cross-sectional view of the zero closure seal taken along the lines 5E-5E of FIG. 5B.
Figure 5F:
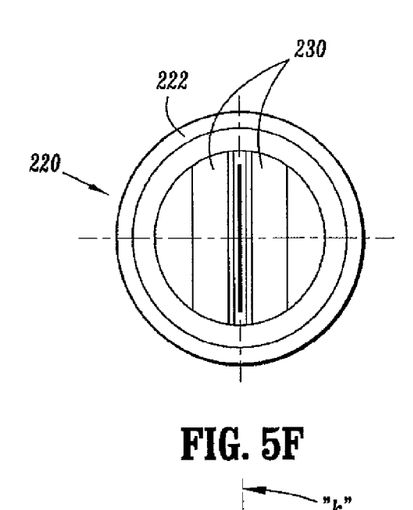
FIG. 5F is a bottom plan view of the zero closure valve.

With reference to FIGS. 5A-5F, zero closure valve 220 is illustrated in detail. Zero closure valve 220 includes outer periphery consisting of collar 222, tapered segment 224 extending inwardly from the collar 222 and second segment 226 extending contiguously from the tapered segment 224. Collar 222 facilitates mounting of zero closure valve 220 within cannula housing 204 by residing on internal shelf 228 of cannula housing 204 (FIG. 4). Collar 222 may or may not be secured to internal shelf 228. Second segment 226 extends in general perpendicular relation to longitudinal axis "a". Zero closure valve 220 further includes first and second lips 230 depending from second segment 226. Lips 230 define lip edges 232 which are in approximated closed relation when the zero closure valve 220 is in the closed position to define slit 234 as depicted in FIGS. 5A-5F. First and second lips 230 each define proximal lip surface 236 which contacts the instrument during its insertion. Proximal lip surface 236 has a curved or arcuate appearance as best depicted in FIG. 5D having a radius of curvature which presents a sloped arrangement approaching lip edges 232. In particular, proximal lip surface 236 defines outer surface portion 238 and inner surface portion 240 interconnected by curved surface 242. Outer surface portion 238 is arranged at a first angle "k" relative to the longitudinal axis "a" and inner surface portion 240 is arranged at a second angle "m". The second angle "m" is preferably less than the first angle "k" to provide a streamlined or sloped appearance shown. In one embodiment, the first angle "k" may range from about 62 degrees to about 73 degrees relative to the longitudinal axis "k", more preferably, about 67 degrees, and the second angle "m" may range from about 37 degrees to about 47 degrees relative to the longitudinal axis "a", more preferably, about 42 degrees. The varied angular arrangement enables the overall length of zero closure valve 220 to be substantially less than in conventional valves. In addition, the narrow angular arrangement of inner surface portion 240 facilitates passage of the instrument by reducing drag and minimizing the forces required to open valve 220. Curved surface 242 may have a radius of curvature ranging from about 0.7 inches to about 0.8 inches more preferably 0.75 inches.

First and second lips 230 may also include ribs 244 extending from proximal lip surfaces 236. Ribs 244 are engaged by the instrument during insertion and provide structural support to zero closure valve 220. Ribs 244 define a space or gap 246 therebetween when zero closure valve 220 is in the closed position. This gap 246 ensures that ribs 244 are free to open and close during insertion and withdrawal of the instrument. Closure valve 220 is preferably adapted to close upon exposure to the forces exerted by the insufflation gases in the internal cavity.

Cannula housing 204 includes at least one locking recess 248 preferably two recesses arranged in diametrical opposed relation. Locking recesses 248 serve to releasably secure seal assembly 100 to cannula assembly 200.

With continued reference to FIGS. 1-4, seal assembly 100 will be discussed in detail. Seal assembly 100 may be a separate component from cannula assembly 200 and, accordingly, adapted for releasable connection to the cannula assembly 200. Alternatively, seal assembly 100 may be incorporated as part of cannula assembly 200. Seal assembly 100 includes a seal housing, generally identified as reference numeral 102, and gimbal mount 104 which is disposed within the seal housing 102. Seal housing 102 houses the sealing components of the assembly and defines the outer valve or seal body of the seal assembly 100. Seal housing 102 defines central seal housing axis "b" which is preferably parallel to the axis "a" of cannula sleeve 202 and, more specifically, coincident with the axis "a" of the cannula sleeve 202. Seal housing 102 incorporates three housing components, namely, first, second and third housing components 106, 108, 110, respectively, which, when assembled together, form the seal housing 102. Assembly of housing components 106, 108, 110 may be affected by any of the aforementioned connection means discussed with respect to cannula housing 204.

First housing component 106 defines inner guide wall 112 and outer wall 114 disposed radially outwardly of the inner guide wall 112. Inner guide wall 112 defines central passage 116 which is dimensioned to receive a surgical instrument and laterally confine the instrument within seal housing 102. As best shown in FIG. 4, inner guide wall 112 defines sloped or tapered portion 118 adjacent its proximal end. Sloped portion 118 is obliquely arranged relative to seal housing axis "b" and extends radially inwardly relative to the seal housing axis "b" in the distal direction. Sloped portion 118 assists in guiding the inserted instrument into central passage 116, particularly, when the instrument is non-aligned or off-axis relative to the seal housing axis "b", or introduced at an angle relative to the seal housing axis "b". Sloped portion 118 provides more flexibility to the surgeon by removing the necessity that the instrument be substantially aligned with the seal housing axis "b" upon insertion. Inner guide wall 112 is generally cylindrical in configuration and terminates in a distal arcuate or rounded surface 120.

Second housing component 108 includes transverse wall 122, inner cylindrical wall 124 depending in a proximal direction outwardly from the transverse wall 120 and outer wall 126 depending in a distal direction outwardly from the transverse wall 120. Inner cylindrical wall 124 is dimensioned to mate with outer wall 114 of first housing component 106, i.e., in a manner to be positioned within the interior of the outer wall 114 in frictional relation therewith. In the alternative, outer wall 114 of first housing component 106 may be adhered to inner cylindrical wall 124 of second housing component 108. Outer wall 126 defines scalloped outer surface 126a which is dimensioned for gripping engagement by the user. Extending contiguously from inner cylindrical wall 124 in the distal direction is an arcuate or cup shaped gimbal wall support 124s which supports gimbal mount 104. Transverse wall 120 further includes intermediate wall 128 of cylindrical configuration, which is disposed between outer wall 126 and gimbal wall support 124s.

Figure 3:
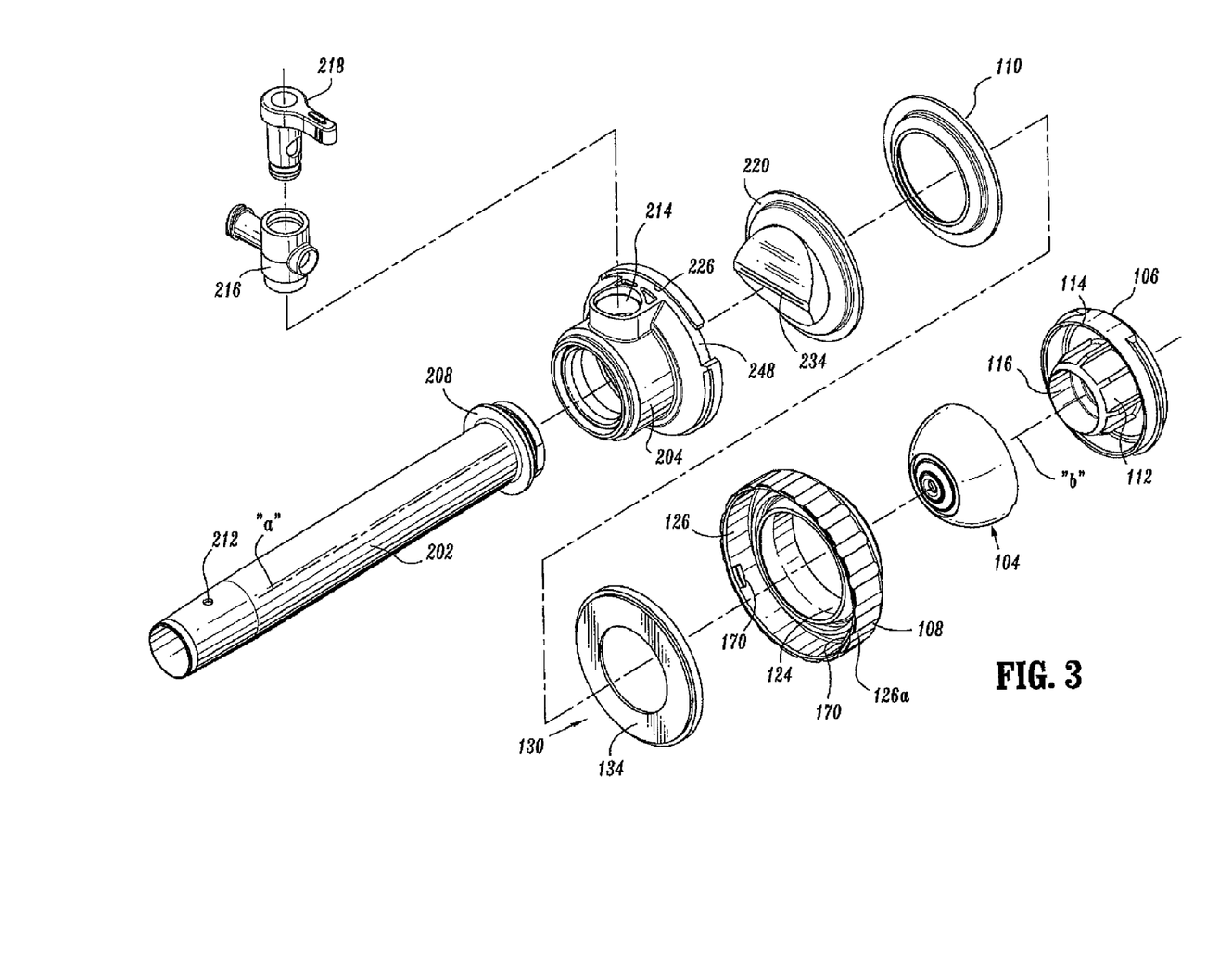
FIG. 3 is a perspective view with parts separated of the cannula and instrument seal assemblies of FIG. 1.
Figure 6A:
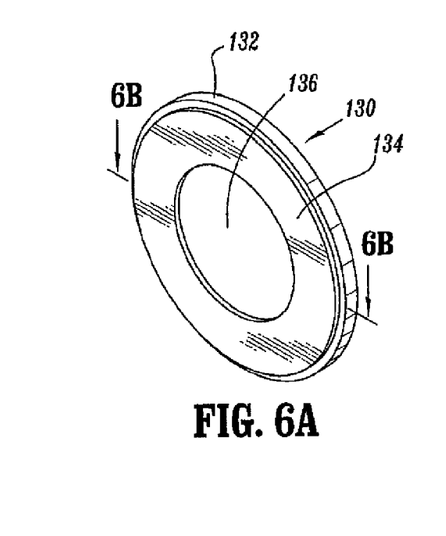
FIG. 6A is a perspective view of the interface seal of the instrument seal assembly.
Figure 6B:
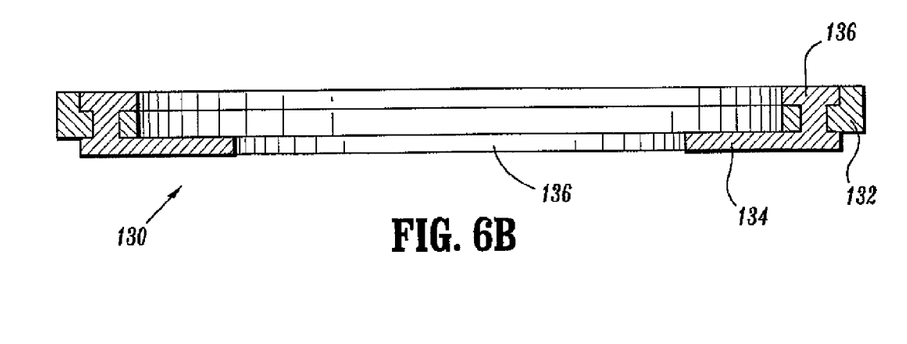
FIG. 6B is a cross-sectional view of the interface seal taken along section lines 6B-6B of FIG. 6A illustrating the interface seal mount and the interface seal member of the instrument seal assembly.
Figure 6C:
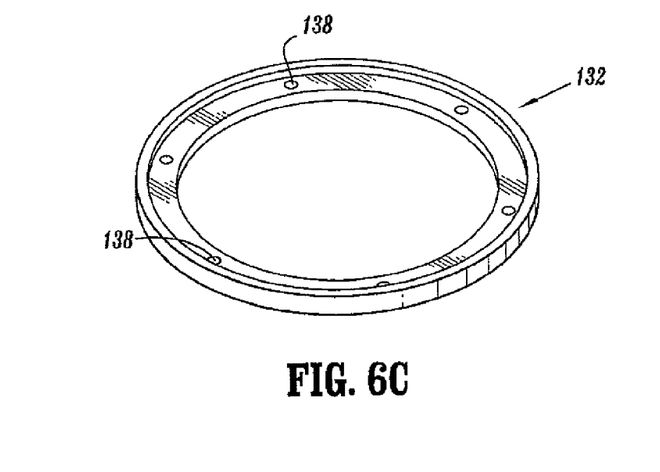
FIG. 6C is a perspective view of the interface seal mount of the interface seal.
Figure 7:
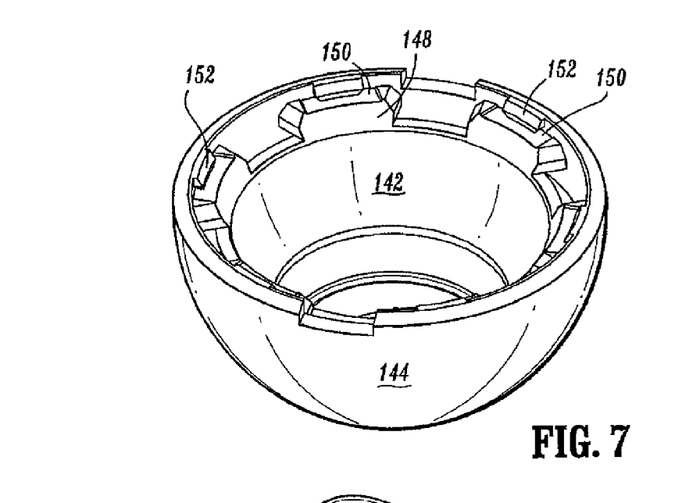
FIGS. 7-8 are top and bottom perspective views of the gimbal mount of the instrument seal assembly.

Referring now to FIGS. 3-4, in conjunction with FIGS. 6A-6C, seal assembly 100 further includes interface seal 130 mounted adjacent gimbal mount 104. Interface seal 130 functions in minimizing the loss of insufflation gases through seal assembly 100. Interface seal 130 includes interface seal mount 132 and flexible interface seal member 134 secured to the seal mount 132. Seal mount 132 is preferably annular in configuration and is fabricated from a relatively rigid material such as a polymeric material or stainless steel. Interface seal member 134 is preferably fabricated from an elastomeric material having qualities to engage seal mount 104 in substantial sealed relation therewith. Interface seal member 134 defines central aperture 136 which receives the forward or distal surface of gimbal mount 104. Interface seal member 134 preferably extends radially inwardly and longitudinally relative to seal housing axis "b" when assembled within seal housing 102. This configuration increases the amount of surface area of interface seal member 134 engaging the outer surface of gimbal mount 104 thereby facilitating the formation and maintenance of a seal about the gimbal mount during manipulation of the instrument. Interface seal 130 further includes gasket seal 136 mounted adjacent the proximal side of interface seal mount 132. Gasket seal 136 is in contact with the forward or distal end of intermediate wall 128 of second housing component 108 and serves to form a seal with the intermediate wall to substantially minimize passage of fluids through seal housing 102.

Interface seal member 134 and gasket seal 136 are preferably monolithically formed of the desired elastomeric material. In one preferred arrangement, interface seal 130 is manufactured via a molding process. In this arrangement, interface seal mount 132 may include a plurality of apertures 138. During molding of interface seal 130, apertures 138 permit the elastomeric material to communicate between the proximal and distal sides of interface seal mount 132 to monolithically form interface seal member 134 and gasket seal 136. Alternatively, gasket seal 136 may be a separate component from interface seal member 134 and may be secured to the seal mount 132 by conventional means.

With particular reference to FIG. 4, gimbal mount 104 is accommodated within an annular space 140 defined between inner and outer walls 112, 114 of first housing component 106. Gimbal mount 104 is mounted in a manner which permits angulation and/or rotational movement of the gimbal mount 104 relative to, or about, seal housing axis "b". Specifically, gimbal mount 104 is free to angulate relative to seal housing axis "b" through a range of motion defined within the confines of annular space 140. The range of movement of gimbal mount 104 will be discussed in greater detail hereinbelow. Interface seal 130 is adapted to maintain a sealing relation with gimbal mount 104 upon angular movement thereof.

Referring now to FIGS. 7-11, in conjunction with FIG. 4, the components of gimbal mount 104 will be discussed in further detail. Gimbal mount 104 includes first and second gimbal housings 142, 144 and resilient seal member 146 which is mounted between the housings 142, 144. In a preferred arrangement, first and second gimbal housings 142, 144 and seal member 146 each define a general hemispherical configuration as shown. First gimbal housing 142 is preferably seated within second gimbal housing 144 and secured to the second gimbal housing 144 through a snap fit connection, welding, adhesives, or the like. Preferably, first gimbal housing 142 includes a plurality of mounting legs 148 radially spaced about the outer periphery of the housing component 134. Legs 148 define locking surfaces 150 which extend in general transverse relation to the axis "b" of seal assembly 200. Similarly, second gimbal housing 144 includes a plurality of corresponding locking detents 152 spaced about the interior of the housing 144. Upon insertion of first gimbal housing 142 within second gimbal housing 144, mounting legs 148 slide along locking detents 152 whereby upon clearing the detents 152, locking surfaces 150 of the mounting legs 148 securely engage the locking detents 152 to fix first gimbal housing 142 within second gimbal housing 144 and secure resilient seal member 146 between the components in sandwiched relation. As appreciated, first gimbal housing 142 is desirably sufficiently resilient to deflect upon insertion to permit mounting legs 148 to clear locking detents 152 and return to their initial position to engage the detents 152.

As mentioned hereinabove, seal member 146 of gimbal mount 104 is interposed between first and second gimbal housings 142, 144. Seal member 146 preferably comprises a resilient center material (e.g., polyisoprene or natural rubber) with first and second layers of fabric 154,156 at the respective proximal and distal surfaces of the resilient material and impregnated with the resilient material. The fabric may be of any suitable fabric for example, a SPANDEX material containing about 20% LYCRA and about 80% NYLON available from Milliken. A suitable seal member or seal type is disclosed in commonly assigned U.S. patent application Ser. No. 09/449,368, filed Nov. 24, 1999, the contents of which are hereby incorporated herein by reference. Seal member 146 defines central aperture 158 for sealed reception of a surgical instrument. In a preferred arrangement, first layer 154 is arranged to extend or overlap into aperture 158. In this manner, the fabric is positioned to engage the surgical instrument upon passage through aperture 158 of seal member 146 thereby protecting the resilient material defining the aperture. This advantageously minimizes the potential of piercing, penetrating or tearing of the resilient material by the instrument. Alternatively, an additional layer of fabric on the proximal surface of seal member 146 may be superposed and arranged to drape within aperture 158. Seal member 146 preferably includes an annular depression 160 on its distal surface, i.e., within second layer 156 of fabric. Depression 160 receives ledge 162 of second gimbal housing 144 to facilitate fixation of seal member 146 between first and second gimbal housings 142, 144.

Figure 8:
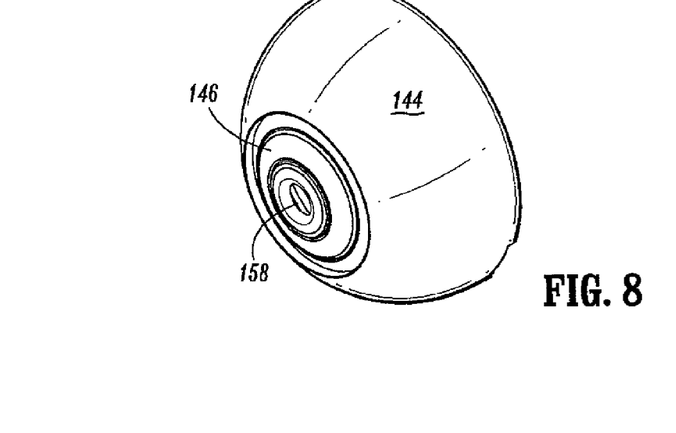
Figure 9:
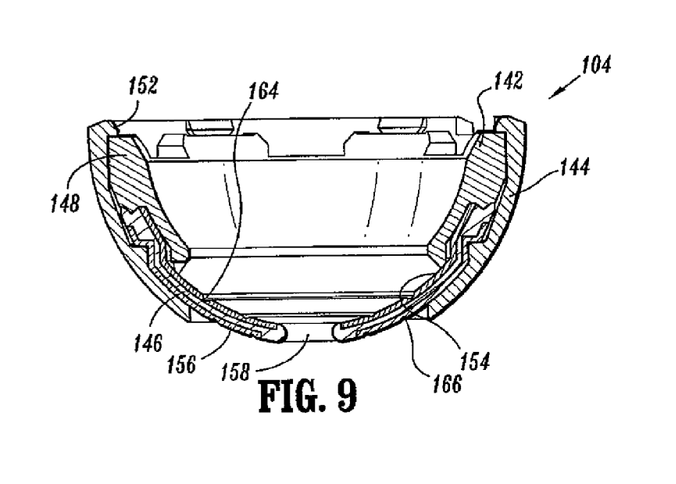
FIGS. 9-10 are cross-sectional views of the gimbal mount.
Figure 10:
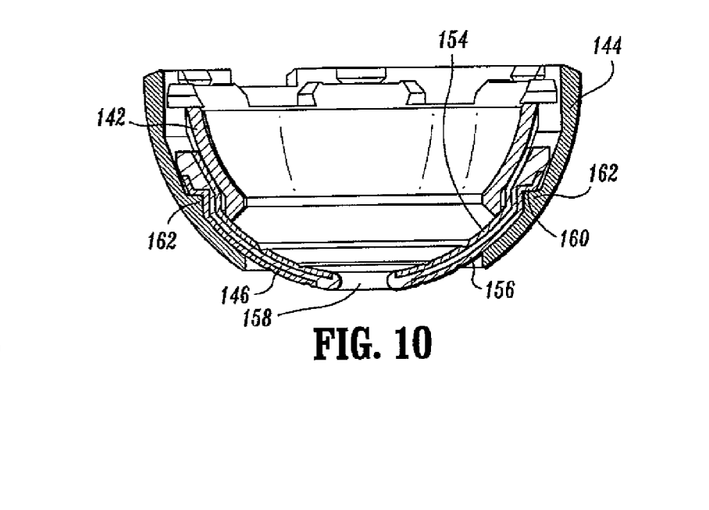
Figure 11:
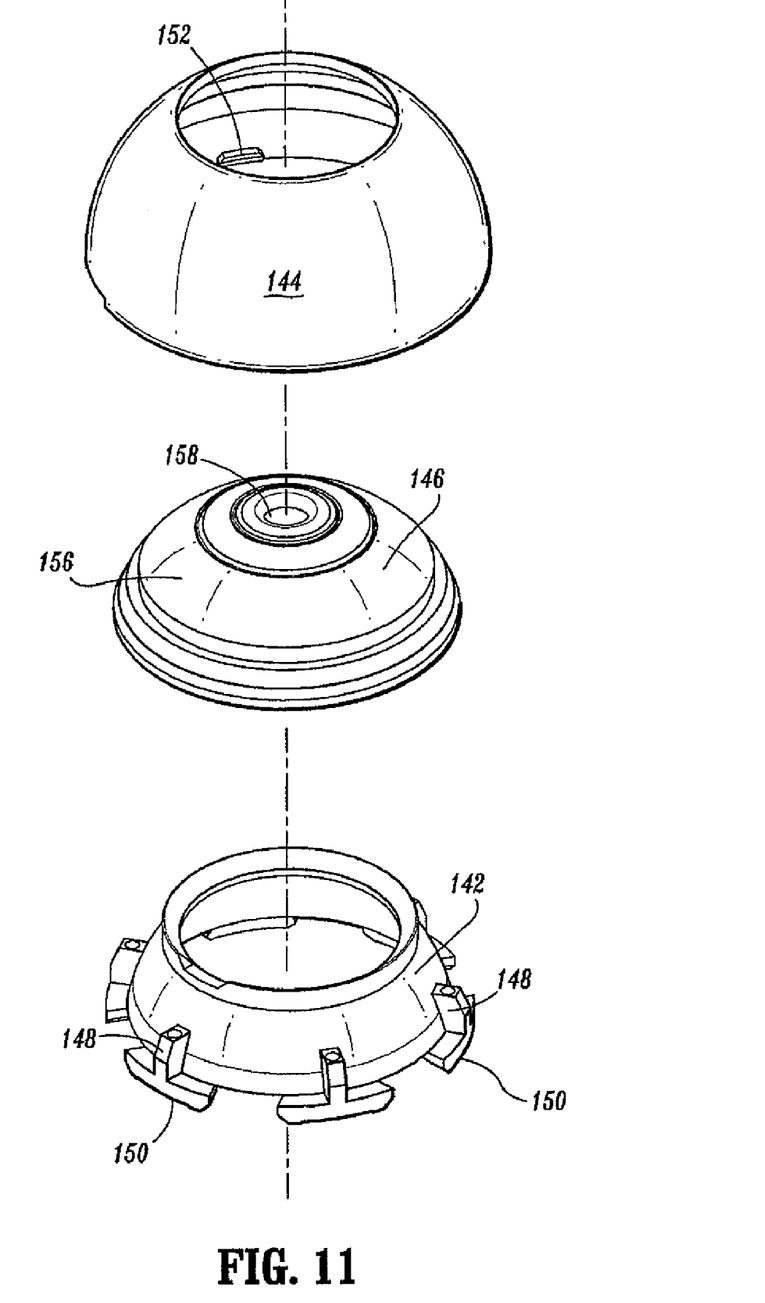
FIG. 11 is a perspective view illustrating the components of the gimbal mount in accordance with the embodiment of FIGS. 1-10.

Although seal member 146 is disclosed as an impregnated fabric arrangement, it is appreciated that other seal types may be used and still achieve the objectives of the present disclosure. Further, FIG. 8 illustrates annular depressions 164, 166 which have been pressed by a molding tool into layer 160. One or more similar depressions may be pressed into layer 160 to assist positioning of fabric during manufacture of seal member 146.

Seal assembly 100 defines a profile or height which is substantially reduced when compared to conventional cannula seal assemblies. In one preferred embodiment, the overall height of seal assembly 100 ranges from about 0.25 inches to about 1.0 inches, preferably, about 0.65 inches. The reduced height provides more operating space above the patient, which is significant, i.e., positioned in the abdomen to access the underlying cavity.

Figure 12:
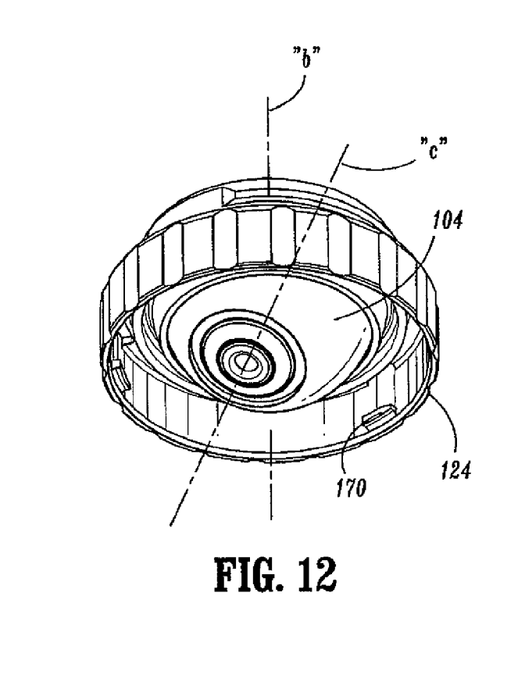
FIGS. 12-14 are perspective views illustrating the range of movement of the gimbal mount within the seal housing.
Figure 13:
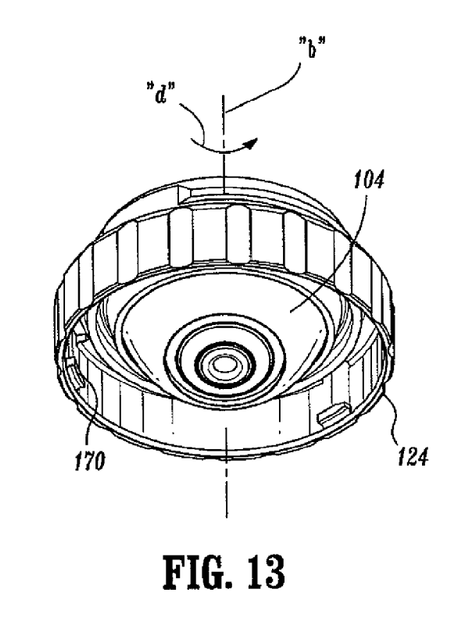
Figure 14:
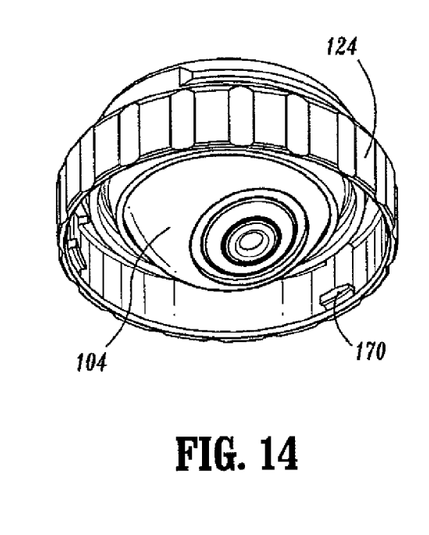
Figure 15:
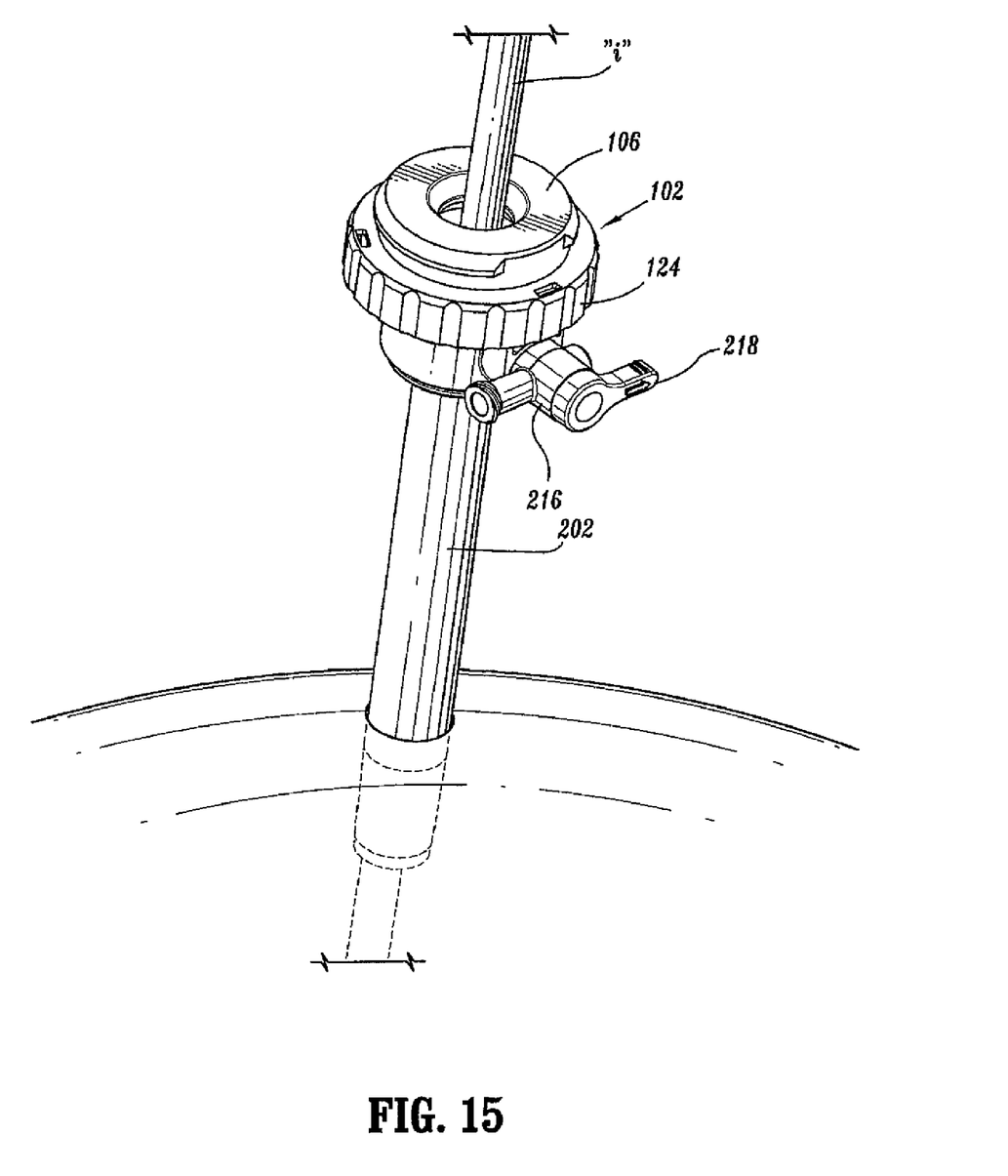
FIG. 15 is a view illustrating the cannula assembly and instrument seal assembly accessing an internal cavity with an instrument introduced therein.

With reference now to FIGS. 12-14, in conjunction with FIG. 4, gimbal mount 104 moves within the annular space 140 defined between inner and outer walls 112,114 to permit angulation of the instrument relative to the seal housing axis "b" and/or rotation about the axis "b" (shown by directional arrow "d") while still maintaining a seal thereabout. During angulation of the instrument, the axis "c" of the aperture 158 of seal member 146 intersects the axis "b" of the seal assembly 100. During angulation, gimbal mount 104 is supported between inner wall 112 and gimbal wall support 124s of seal housing 102. The arcuate inner surface of first gimbal housing 142 rides along distal arcuate surface 120 of inner wall 112 in contacting relation therewith to permit gimbal mount 104 to swivel within seal housing 102. Interface seal member 134 of interface seal 130 permits angular movement of gimbal mount 104 while maintaining the substantial sealing relation with the outer surface of second gimbal housing 144. Lubricant may be provided on the appropriate surfaces to facilitate angulation. In a preferred arrangement, gimbal mount 104 may angulate through an angle inclusive of about 30°, more preferably about 22.5° relative to seal housing axis "b".

Seal assembly 100 may be associated with, or joined to, cannula assembly 200 in a variety of ways. In a preferred embodiment, seal housing 102 of seal assembly 100 and cannula housing 204 of cannula assembly 200 are adapted to detachably engage each other, e.g., through a bayonet lock, threaded connection, or like mechanical means. In one preferred embodiment, second housing component 108 of seal housing 102 includes a plurality of ribs 170 depending radially inwardly from outer wall 24 (FIG. 3). Ribs 170 are received within locking recesses 224 of cannula housing 204, and seal assembly 100 is rotated to secure the ribs 170 beneath the outer wall 226 of cannula housing 204. Other means of joining seal assembly 100 to cannula assembly 200 will be readily apparent to one of ordinary skill in the art.

Figure 16:
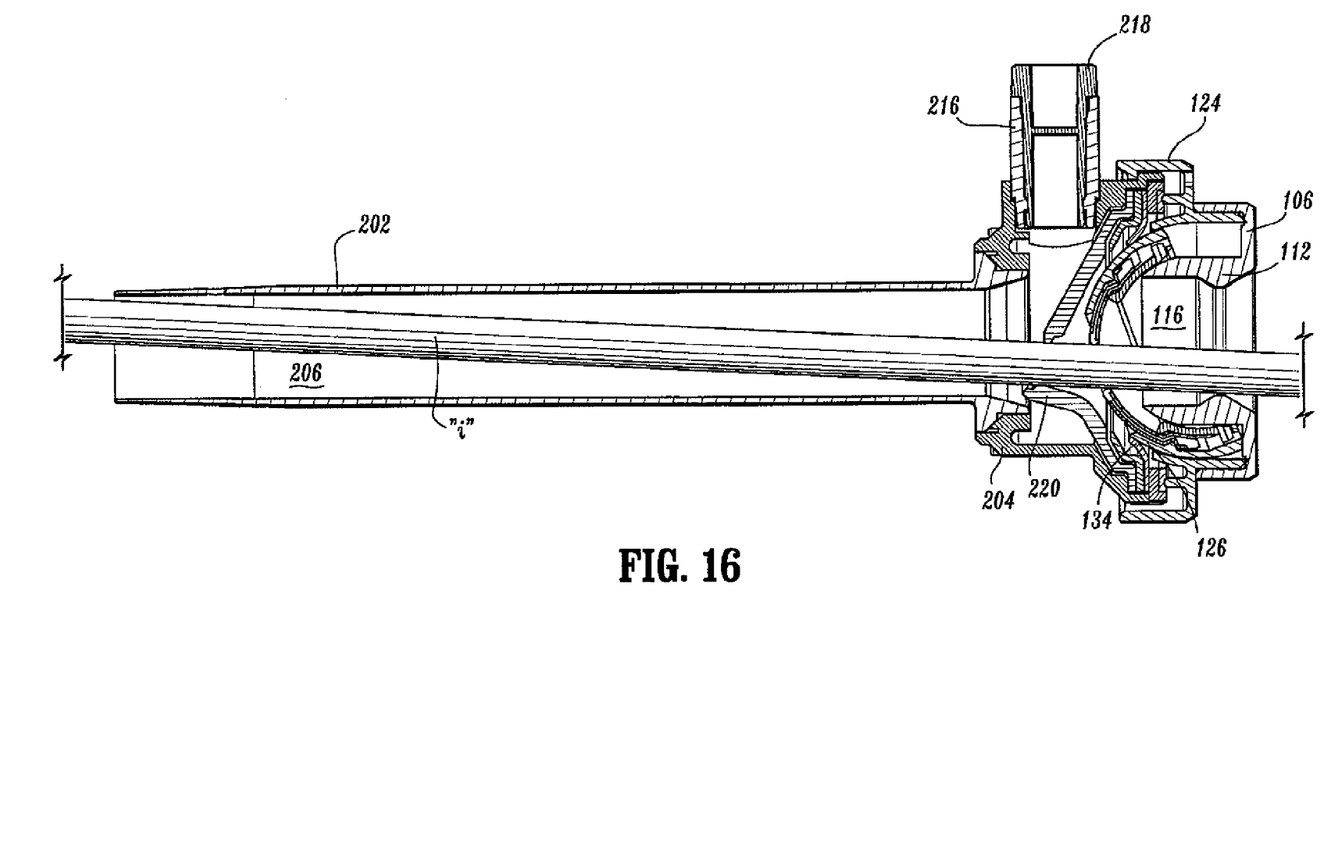
FIG. 16 is a side cross-sectional view of the cannula and instrument seal assemblies illustrating a range of movement of the surgical instrument.

Referring now to FIG. 16, use of the seal assembly 100 and cannula assembly 200 in connection with introduction of a surgical instrument will be discussed. Seal assembly 100 is mounted to cannula assembly 200 which may or may not be previously introduced into an insufflated abdominal cavity. An instrument "i" is inserted into seal assembly 100 through passage 116 of inner cylindrical guide wall 112 in seal housing 102. If the axis of the instrument is not perfectly aligned with the axis "a" of cannula assembly 200 or axis "b" of seal assembly 100, then the surgical instrument will contact sloped portion 118 of inner guide wall 112 and/or the inner surface of the seal member 146. Sloped portion 118 guides the instrument into seal housing 102. Contact with seal member 142 can cause some deformation of the seal member 142. The instrument "i" slides along the surface of the gimbal mount 104 and/or the seal member 142 to the aperture 154. The inner seal portions defining aperture 154 stretch to accommodate the instrument diameter, as necessary. The instrument "i" is advanced through aperture 158 of seal member 146 whereby portions of the seal member 146 defining the aperture 158 engage the instrument "i" in sealed relation therewith. The instrument "i" passes further distally into the cannula housing 204 passing through duckbill valve 216 and cannula sleeve 202 into the body cavity. The instrument "i" may be manipulated within seal housing 102 and cannula housing 204. Once the instrument "i" is disposed within the aperture 154, and the friction at the interface seal member 134, gimbal mount 104 and sloped portion 118 is overcome, gimbal mount 104, swivels with respect to seal housing 102 as the instrument is manipulated. Gimbal mount 104 is free to swivel relative to housing 102, while allowing seal member 142 to maintain sealing engagement with the instrument "i" passed therethrough, as well as maintaining the seal around the gimbal mount 104. Preferably, the seal member 142 includes resilient material and fabric material which resists deformation of the aperture 154, as well as tearing of the seal member 142. As discussed, the instrument "i" may be rotated about seal housing axis "b" or pivoted relative to the axis "b" as desired via gimbal mount 104 to perform the surgical procedure. During these manipulations, interface seal member 134 of interface seal 130 maintains a sealing relation with gimbal mount 104.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed:

1. A surgical access assembly for use with a surgical access device, which comprises:

a housing defining a central longitudinal axis;

an elongate access member extending from the housing, the housing and the access member having a longitudinal passage dimensioned to permit passage of a surgical instrument and defining proximal and distal ends; and a zero closure valve mounted relative to the housing and being adapted to assume an open condition upon passage of the surgical instrument and a substantially closed position in the absence of the instrument, the zero closure valve including a valve periphery having a collar, a tapered segment extending inwardly from the collar and a second segment extending contiguously from the tapered segment, first and second lips depend from the second segment of the zero closure valve and define lip edges which are in approximated closed relation when the zero closure valve is in the closed position to define a slit, the first and second lips each including a proximal lip surface having an outer surface portion and an inner surface portion interconnected by a curved surface, wherein a support rib depends from the proximal lip surface of each of the first and second lips to define a gap therebetween to be in spaced relation when the valve is in the closed position and being positioned to contact the surgical instrument during insertion through the first and second lips.

2. The surgical access assembly according to claim 1 further including an instrument seal disposed within the housing and being adapted to establish a substantial fluid tight seal about the instrument.

3. The surgical access assembly according to claim 1 wherein the second segment extends in a generally perpendicular relation to the central longitudinal axis.

4. The surgical access assembly according to claim 1 wherein the outer surface portion is arranged at a first angle relative to the longitudinal axis.

5. The surgical access assembly according to claim 4 wherein the inner surface portion is arranged at a second angle relative to the longitudinal axis.

6. The surgical access assembly according to claim 5 wherein the second angle is less than the first angle.

7. The surgical access assembly according to claim 5 wherein the first angle is between about sixty-two degrees (62°) to about seventy-three degrees (73°) relative to the central longitudinal axis.

8. The surgical access assembly according to claim 5 wherein the first angle is sixty-seven degrees (67°) relative to the central longitudinal axis.

9. The surgical access assembly according to claim 5 herein the second angle is between about thirty-seven degrees (37°) to about forty-seven degrees (47°) relative to the central longitudinal axis.

10. The surgical access assembly according to claim 5 wherein the second angle is forty-two degrees (42°) relative to the central longitudinal axis.

11. The surgical access assembly according to claim 1 wherein the curved surface includes a radius of curvature ranging from about 0.7 inches to about 0.8 inches.

12. The surgical access assembly according to claim 11 wherein the radius of curvature is 0.75 inches.

* * * * *